United States Patent [19]

Pirschel

[11] Patent Number: 4,545,385

[45] Date of Patent: Oct. 8, 1985

[54] ULTRASOUND EXAMINATION DEVICE FOR SCANNING BODY PARTS

[75] Inventor: Joerg Pirschel, Tuebingen, Fed. Rep. of Germany

[73] Assignee: Siemens Aktiengesellschaft, Munich, Fed. Rep. of Germany

[21] Appl. No.: 477,039

[22] Filed: Mar. 21, 1983

[30] Foreign Application Priority Data

Mar. 23, 1982 [DE] Fed. Rep. of Germany ....... 3210610
Jan. 24, 1983 [DE] Fed. Rep. of Germany ....... 3302254

[51] Int. Cl.$^4$ ............................................. A61B 10/00
[52] U.S. Cl. ..................................... 128/660; 73/620
[58] Field of Search .................. 128/660; 73/618-620, 73/642, 644

[56] References Cited

U.S. PATENT DOCUMENTS

| 3,603,303 | 9/1971 | Stouffer . | |
|---|---|---|---|
| 3,854,471 | 12/1974 | Wild | 128/660 |
| 4,063,097 | 12/1977 | Barrett et al. . | |
| 4,105,018 | 8/1978 | Greenleaf et al. . | |
| 4,130,112 | 12/1978 | Frazer . | |
| 4,167,180 | 9/1979 | Kossoff | 128/660 |
| 4,206,763 | 6/1980 | Pedersen | 128/660 |
| 4,222,274 | 9/1980 | Johnson | 128/660 X |
| 4,252,125 | 2/1981 | Iinuma | 128/660 |
| 4,317,369 | 3/1982 | Johnson . | |
| 4,338,948 | 7/1982 | Perez-Mendez et al. | 128/660 |
| 4,341,222 | 7/1982 | Gardineer et al. | 128/660 |
| 4,362,058 | 12/1982 | Abele | 128/660 X |
| 8,000,193 | 2/1980 | Dick et al. . | |

FOREIGN PATENT DOCUMENTS

| 2314328 | 7/1976 | Fed. Rep. of Germany . |
| 2908248 | 3/1979 | Fed. Rep. of Germany . |
| 3002067 | 1/1980 | Fed. Rep. of Germany . |
| 2425837 | 5/1978 | France . |
| 2015732 | 3/1978 | United Kingdom . |

Primary Examiner—Kyle L. Howell
Assistant Examiner—Francis J. Jaworski
Attorney, Agent, or Firm—Mark H. Jay

[57] ABSTRACT

Medical apparatus for ultrasonic examination of body parts which includes a fluid container and an ultrasound scanning system which is removably coupled to the fluid container. The fluid container serves as an efficient ultrasound conducting medium. Support and rotation means allow scanning of the body part from a plurality of directions.

30 Claims, 9 Drawing Figures

ULTRASOUND EXAMINATION DEVICE FOR SCANNING BODY PARTS

BACKGROUND OF THE INVENTION

The invention relates to an apparatus designed to examine body parts, in particular mammaries and testicles, with ultrasound.

Equipment of this type serves especially for the examination of mammaries (ultrasound mamma diagnosis). In a typical setting, the female breast is immersed into a fluid container. An ultrasound scanning system which is mounted within the fluid container is used for obtaining scans of inner surfaces of the breast. The fluid serves as an efficient ultrasound energy transmitting medium.

Because the ultrasound scanning system is immersed in a fluid, special problems related to sealing an electrical insulation are present. Additionally, the ultrasound scanning system is an integral component of the examination apparatus and as such is not available for other generalized use.

SUMMARY OF THE INVENTION

An object of this invention is to create a configuration which does not create sealing and electrical insulation problems with respect to an ultrasound scanning system. As a further objective, an ordinary ultrasound realtime echo system is allowed to be retrofitted for mammasonography, that is a supplementary system is created, which enables quantitative mamma diagnostic procedures in conjunction with presently marketed ultrasound systems for realtime image display.

According to the invention, an ultrasound scanning device is now situated in a second container and therefore outside the fluid container. Consequently, the ultrasound scanning device does not require special sealing procedures and the electrical insulation problems have been eliminated as well. Any presently marketed ultrasound scanning device can be applied, which can be easily exchanged and used, if necessary, in other locations. The specific placing of the ultrasound scanning device into the second container and the possibility of a 360° rotation together with the second container have led to the ability to scan an unlimited number of slices with one single complete rotation around the entire body part, i.e. the female breast or the testicles.

Additional advantages of the invention are described below.

In one embodiment, the body part to be examined extends into the liquid of the fluid container and the entire system rotates without requiring the relative motion between the ultrasound scanning system and the fluid container, which disturbs the coupling of the former onto the latter. In yet another embodiment, the body part to be examined is immersed only indirectly into the liquid of the fluid container via a membrane, which has been stretched across the entrance opening of a cover board. This is advantageous insofar as the immersing body part does not come in direct contact with the liquid and that a frictionless rotation of the entire system remains possible, which is comprised of the fluid container, the second container and the ultrasound scanning system placed therein. However, there would be constant friction between the membrane and the body part to be examined during the rotation procedure, if the rotating fluid container is provided with a membrane stretched directly across its container opening. Therefore, a fluid container which has been provided with a membrane stretched directly across its container opening is only useful, when the container remains stationary, whereby, however, the problem of the relative motion between the rotating ultrasound scanning system and the stationary fluid container will recur.

In an embodiment which solves the above problem, a system is described in which the fluid container which is covered with the membrane is allowed to remain stationary. To obtain the different scan perspectives, an ultrasound array rotates around the fluid container. A support rod device supports the ultrasound array of the scanning system so that the array is ultrasonically coupled to the fluid container while rotating around it. Other features and advantages of the invention will be apparent from the following description of the preferred embodiments, and from the claims.

For a full understanding of the present invention, reference should now be made to the following detailed description of the preferred embodiments of the invention and to the accompanying drawings.

DESCRIPTION OF THE PREFERRED EMBODIMENTS

Figure 1:
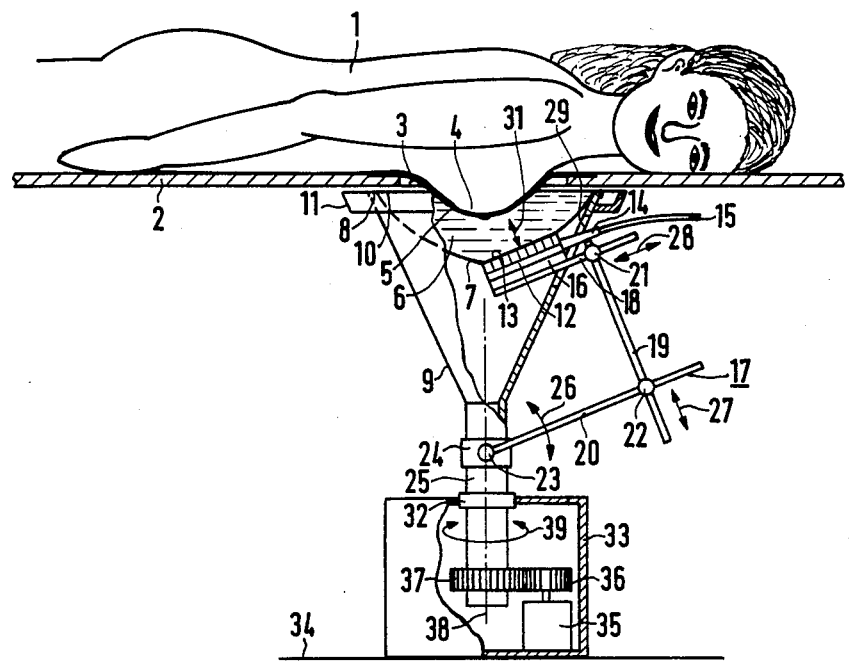
FIG. 1 depicts a first, preferred sample embodiment of the invention applied to ultrasound mammasonography.

In FIG. 1. a patient 1 is lying on a cover board 2, which may be part of a patient table. The cover board 2 includes an entrance opening 3, over which a membrane 5, has been stretched. The patient 1 lies on the cover board 2 in such a manner as to place the breast to be examined 4 on the membrane 5 of the entrance opening 3. As illustrated, the breast's 4 own weight causes the membrane 5 to be pushed through the entrance opening 3 of the cover board 2. During this process, the membrane 5 lies against the surface of breast 4.

How far the breast 4 will extend through the entrance opening 3 of the cover board 2 depends on the degree of flexibility of the membrane. Depending on the case to be examined, more or less flexible membranes can be applied. Especially during tumor examination, it is recommended to use rubber foil as a membrane, which compresses the breast to a predetermined degree. Plastic foil can be used as well. However, its poor elasticity will result in a stronger compression of breast 4. Likewise, material such as used for nylon stockings or gauze can be applied. Because of the liquid seeping through from the liquid-filled basin underneath, an acoustic coupling is generated. Tumors can be better differentiated in a compressed breast than in a freely immersed breast 4. Different degrees of flexibility can be achieved by using exchangeable membranes of materials of varying flexibility. However, they can be also achieved by continuously using the same material for the membrane. Toward this end, an appropriate stretching mechanism for the membrane 5 has to be provided. With the aid of this stretching mechanism, the membrane 5 can be stretched in such a manner as to enable examinations ranging from a completely relaxed breast during free immersion to a slightly or strongly compressed breast. When applying the depicted configuration to testis sonography, the stretching mechanism enables an examination of freely immersed testicles during complete relaxation or removal of the membrane 5.

The sample embodiment of FIG. 1 is the actual system configuration to examine the breast 4 with ultrasound below the entrance opening 3 for the breast 4 in cover board 2. The system is comprised of a fluid container 6. Its flexible wall or skin 7 is attached, at the outer upper edge 8 of a support device 9 having the shape of a funnel, so that the support device 9 surrounds the fluid container 6. The skin 7 consists of a thin foil or a hemispherically shaped membrane of an efficient ultrasound conducting or at least ultrasound transmitting material, such as plastic material or synthetics such as PVC or rubber. Purchasable synthetic shower caps were used for testing purposes.

The fluid container 6 and the funnel-shaped support configurations have been provided with top openings. The water level in the fluid container 6 has to be such as to reach up to the container and/or funnel opening when a breast 4 is immersed therein. Overflowing water can be collected in a collecting container, an overflow groove 11 or an overflow container.

In order to scan the breast 4, an ultrasound transducer is used, preferably a multi-element ultrasound transducer and specifically a linear array with an ultrasound radiation surface 13 and a connection bush 14 for the signal cable 15. The ultrasound array 12 is part of a commercially marketed sonographical examination device with realtime display, i.e. part of Siemens device "Sonoline 8000." In principle, an ultrasound scanning system of the type having a mechanical scanner can be used as well, such as a currently used sector scanner. The position of the individual elongated ultrasound elements of an array have been illustrated in FIG. 3. The ultrasound array 12 for example has a width of 10 cm and an ultrasound frequency of 3.5 MHz. It is arranged on a U-shaped support rail 16, which is attached to a support rod device 17. The support rod device 17 consists of three rod parts 18, 19, 20. The rod parts 18 and 19 are connected via a first cross joint 21, while the rod parts 19 and 20 are connected via a second cross joint 22. The lowest part of the rod part 20 is attached to a sleeve 24 by means of a swivel joint 23. In turn this sleeve 24 sits at the shaft of a rotary selector 25, which is the lower part of the funnel-shaped support device 9. With the aid of the swivel joint 23, the entire support rod device 17 can be moved in direction of the double arrow 26. The second cross joint 22 is designed in such a manner as to enable the rod part 19 to be moved in the direction of the double arrow 27. Accordingly, the rod part 18 with the U-shaped support rail 16 for the ultrasound array 12 can be moved with the aid of the first cross joint 21 in the direction of the double arrow 28.

Figure 2:
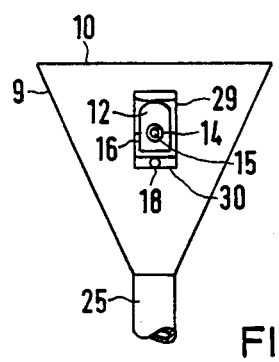
FIG. 2 illustrates the funnel-shaped support configuration shown in FIG. 1, but from a 90° angle.

As illustrated in FIG. 2, the U-shaped support rail 16 for the ultrasound array 12 can be inserted into the interior of support device 9 via an opening or a slot 29 in the wall of the support device 9. In doing so, the rod part 18 lies in a mobile mode on the lower edge 30 of the slot 29. Therefore, according to the setting of the support rod 17 and via the the slot 29, the U-shaped support rail 16 together with the embedded ultrasound array 12 can be brought into a desired coupling position at the fluid container 6 in the support device 9. The illustrated coupling location of the ultrasound array 12 is of special interest with respect to this sample embodiment. With this coupling location, the ultrasound array 12 lies below a predetermined angle, that is to say, it is in a more or less tilted position at the fluid container 6, so that the radiation surface 13 of ultrasound array 12 is essentially perpendicular to the surface of the compressed breast 4. Therefore, the cone shape of the breast 4 is reconstructed during rotation. With it a cone-shaped scanning motion of the radiation surface 13 results, which is especially important for an optimal axial and especially lateral resolution ability. The process of vertical acoustic irradiation is indicated by the double arrow 31 in FIG. 1.

According to FIG. 1, the rotary selector 25 of the funnel-shaped configuration is mounted by means of a pivot bearing 32 on the surface of a housing 33. The housing 33 is located on a floor base 34 below the cover board 2 of the patient table. However, instead of being located on the floor base 34, the housing 33 can also be located on an inserted auxiliary shelf 47, which in turn has been attached to the cover board 2 of the patient table. This application possibility has been indicated in FIG. 5.

The housing 33 includes an electrical motor 35. The rotary selector of the motor 35 interfaces via a first toothed wheel 36 with a second toothed wheel 37 at the lower end of the rotary selector 25 of the support device 9. As soon as the motor 35 has been switched on, the support device 9 together with the fluid container 6 and the ultrasound array 12 coupled thereto are continuously turned or swiveled around a central rotation axis 38 via the toothed wheel gearing 36, 37, and the rotary selector 25. This swivel process includes a 360° turn into one direction of rotation and a 360° turn into the opposite direction of rotation to return to its original position. This process has been indicated by the double arrow 39. While the system is turning, the ultrasound array 12 scans the breast 4 in a plurality of cross sections with ultrasound in accordance with the pulse/echo principle. The accumulating echo signals from the various slice planes of the breast 4 are in the form of continuously changing echo slice images drawn as usual onto a (not shown) image display unit, especially equipped with a cathode ray tube to which the ultrasound array 12 has been attached via the signal cable 15. This continuous image is more favorable for evaluation purposes than a sequence of static slice images.

Therefore, with a single 360° rotation the female breast can be scanned in a plurality of slices with the scanning configuration depicted in FIG. 1 The entire system rotates, consisting of fluid container 6, support device 9 together with the ultrasound array 12. Because of the tilted position of the array 12 to the rotation axis 38, a motion of the ultrasound transducer on a cone shell-shaped scanning path results. Practically no friction problems occur between the water of the fluid container 6 and the breast 4 coupled via the membrane 5. Since the ultrasound array 12 is located outside the fluid of the fluid container 6, the ultrasound array does not require additional sealing, and no electrical insulation problems with respect to the signal cable connection will be present. As already mentioned, the ultrasound array 12 is a commercially available product. This is advantageous, because it can be exchanged any time as well as applied toward other application purposes.

The cover board 2, the fluid container 6, the support device 9 and the drive of the ultrasound array 12 have to be considered as a supplementary device for the ultrasound array 12. That is to say, that an already existing ultrasound array 12 can be retrofitted with this additional device for application with mammasonography.

Figure 3:
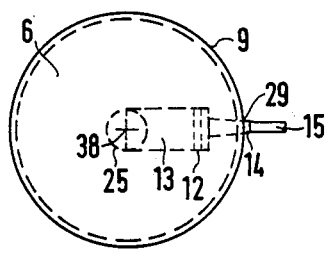
FIG. 3 provides a top view of the funnel-shaped support configuration used in FIG. 1.

FIG. 3 shows a top view of the scanning device. The entered reference numbers for the depicted components correspond with those of FIG. 1.

Figure 4:
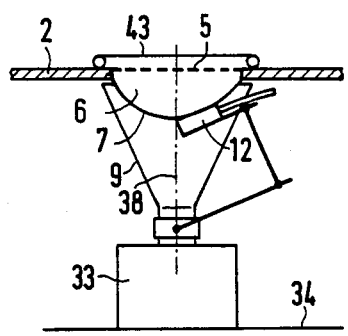
FIG. 4 shows a second sample embodiment of the invention, wherein an ultrasound array travels around the perimeter of a stationary fluid container.

FIG. 4 depicts an additional solution insofar as the fluid container with its skin 7 is no longer attached to the upper edge of the funnel-shaped support device 9, but instead is attached to the opening 3 of the cover board 2. Therefore, the fluid container 6 is now stationary. The funnel-shaped support device 9 could be completely eliminated here. It serves the present case merely as a rotating, protective device. Accordingly, the ultrasound array 12 at the coupling location rotates relative to the fluid container around the rotation axis 38.

When using an embodiment as illustrated in FIG. 4, wherein the fluid container 6 is stationary, it is recommended to use a perforated or similarly designed membrane as membrane 5 to couple the breast to the fluid of the fluid container 6. Perforation or similar measures enable on one hand that the fluid container 6 can be filled with a random amount of water, and on the other hand, that a possible overflow of water caused by the immersion of the breast 4 together with membrane 5 into the stationary fluid container 6 can be drained off through the perforation or similar measures. In order to collect the overflowing water, preferably a small, inflatable rubber ring 43 is located concentrically to the entrance opening 3 on the cover board 2. The overflowing water is collected in the interior of this ring 43, when the patient immerses the breast 4 together with the membrane 5 through the ring 43 into the water of the fluid container.

Furthermore, the inflatable rubber ring provides, in addition, an especially soft positioning of the breast part. Of course, such a ring 43 can also be used with the configuration shown in FIG. 1. Equally, the membrane 5 of FIG. 1 can have a perforated design, if such is required. Again, the ring 43 will then simultaneously serve as a collecting container for the overflowing water. However, if membrane 5 is not perforated, that is to say waterproof, the fluid container 6 should only be filled with a body of water which causes no or only minimal water overflow during the immersion of the breast.

Figure 5:
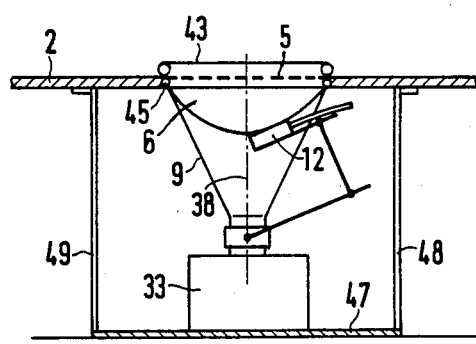
FIG. 5 provides a third sample embodiment of the invention.

FIG. 5 shows an additional solution. Again the fluid container 6 is permanently attached to a funnel-shaped support device. However, the support device 9 is attached in a rotating mode on its upper edge in the entrance opening 3 or below this opening 3 to the cover board 2 by means of a ring-shaped ball bearing 45. In this sample embodiment support device 9 and fluid container 6 are rotated again together with the coupled ultrasound array 12 around the rotation axis 38. As before, the membrane 5 can be perforated and the ring 43 can serve as a collecting container for the overflowing water. As an important feature, the entire scanning configuration is located on an auxiliary shelf 47, which has been attached by means of support bars 48, 49 or a similar device to cover board 2 of the patient table.

Figure 6:
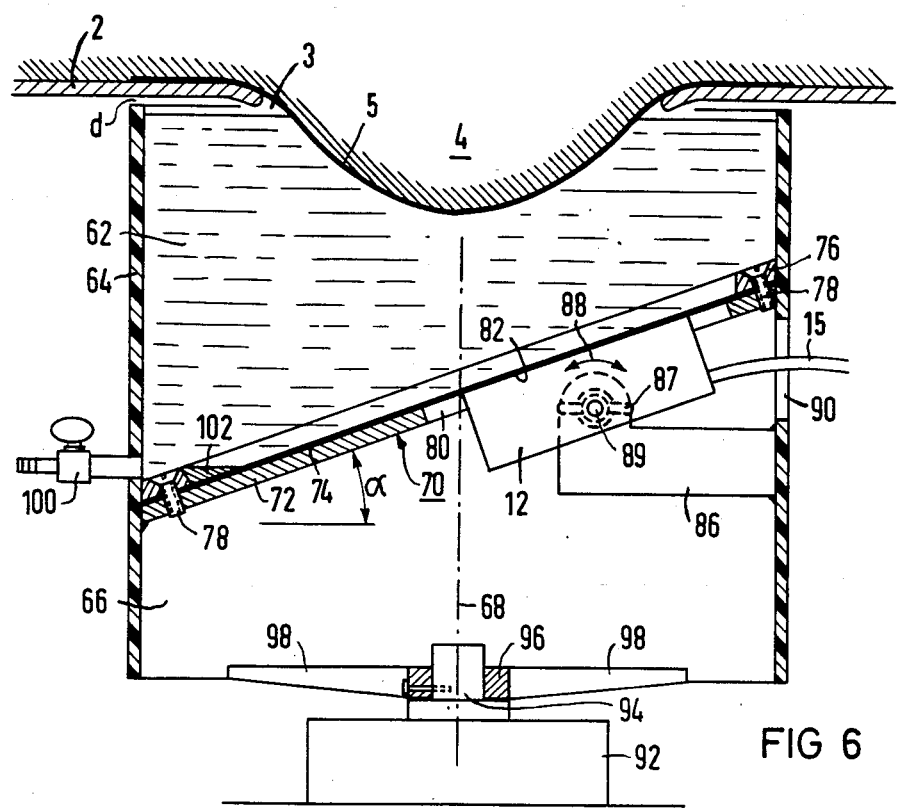
FIG. 6 shows a fourth sample embodiment of the invention, whereby the fluid container has been designed as a cylindrical body with a slanted separation wall.
Figure 7:
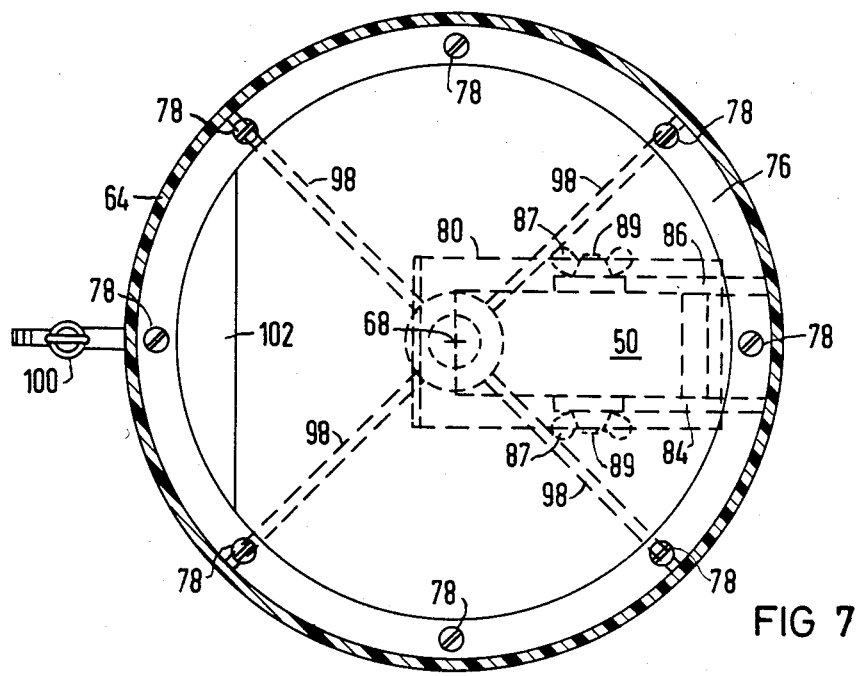
FIG. 7 provides a top view of a supplementary configuration according to FIG. 6.

FIG. 6 and 7 depict another configuration to be used with commercially marketed realtime ultrasound examination devices. The realtime ultrasound examination device is known as such and is not shown. Only its scanning head 50 with signal cable 15 are illustrated. The supplementary configuration has been especially designed for routine examinations of the female breast.

The patient is placed on a patient cover board 2, which has been provided with an entrance opening 3. A flexible membrane 5, preferably a rubber membrane, has been stretched across the entrance opening 3. The breast 4 of the patient lies closely against the surface of membrane 5 and will be compressed to a certain degree by the membrane 5. It is to be noted, that the membrane 5 will take on the shape of the compressed breast 4. No contact or coupling medium, such as gelate, need be present between the membrane 5 and the breast 4.

During the examination, the membrane 5 is immersed from above into the liquid-filled basin, which is located in the upper container 62. Water is preferred for its efficient ultrasound conducting properties. The upper container 62 is formed by a cylindrical body or cylinder 64, which also includes a lower expanse or container 66. The cylindrical body 64 has been arranged at a relatively short distance d from the underside of the cover board 2. The cylinder 64 has a relative wide and flat shape. Preferably, it is manufactured from a synthetic material. As it will be detailed later, the cylindrical body 64 rotates during the examination around its cylinder or longitudinal axis 68, which is in vertical position during the examination.

A slanted, liquid resistant separation wall 70 has been inserted into the cylinder 64. This separation wall 70 divides the interior of the cylinder into the upper and lower container 62 and/or 66. It can be said that with this construction the lower container 66 "carries" the upper container 62. The separation wall includes a floor 72 of a relative stable material (i.e. synthetics or metal), the surface of which is covered with a flexible foil 74. This foil 74, preferably made of rubber, is attached in a liquid-resistant mode at the inner edge of the cylinder 64 by means of an elliptic fastening ring 76. This fastening ring 76 is pressed by means of a suitable fastening device, i.e. screw couplings 78, against the edge of the foil 74. As an alternative, an adhesive connection between the foil 74 and the floor 72 can be selected. As mentioned, the floor 72 can be of a synthetic material. The floor can be either glued or welded into the cylinder 64.

The floor 72 and therefore also the foil 74 are tilted by an angle in relation to the horizontal. As tests have shown, this angle can be approx. 20° for many applications. Therefore, the tilting angle between cylinder axis and the separation wall measures approximately 70°.

The floor 72 has a rectangular recess, in the center of which the ultrasound array 12 has been arranged. In this case, it can be a conventional ultrasound array with a nearly rectangular front end or radiation and receiving surface 82 for realtime image display, operating according to the pulse/echo principle. Consequently, a linear array of ultrasound converter elements of conventional configuration is preferred. As can be seen from FIG. 2, a defined distance has been provided between the edges of the nearly rectangular radiation surface 82 and the edges of the rectangular recess 80 respectively.

In relation to the horizontal, the rectangular radiation surface 82 of the ultrasound array 12 is tilted approx. by an angle α. The radiation surface 82 is located in the lower container 66 and lies against the underside of foil 74. The ultrasound array is supported by two angle brackets 84 and 86, the ends of which are nonflexibly connected in the lower container 66 to the interior wall of cylinder 64. In this instance, the ultrasound array can be manually loosened by means of the winged bolts 87 and inclined or swivelled around a horizontal axis 89, as indicated by double arrow 88. By inclining the ultrasound array 12 around this axis 89, the radiation surface 82 lying against the foil 74 can be adjusted parallel to the skin surface of breast 4. The degree of tilting can be relatively small and can measure only a few degrees, because the coarse adjustment has already been achieved to a large extent by the previously mentioned arrangement of the floor 72 below the angle (90°) with respect to the vertical (cylinder axis 68). During tilting with the described angle, the rubber foil 74 will be slightly stretched on one side.

As already mentioned, a fastening device which can be loosened, such as a bolted joint with winged bolts 87 has been provided for securing and tilting around the horizontal axis 89. By means of this bolted joint the ultrasound array 12 has been tightly secured, but can always be loosened with the angle brackets 84, 86 and, therefore, connected with cylinder 64. After the angle brackets 84, 86 have been unscrewed, the ultrasound array 12 can be used for other purposes than mammasonography. Toward this end, the ultrasound array 12 and the signal cable 15 are removed through a cylinder opening 90 in the lower cylinder wall.

A driving motor 92 has been provided for the continuous drive of cylinder 64. The rotation around the cylinder axis 68 can extend over an angle of $+/-360°$. The driving axis 94 of the driving motor 92 is located coaxially to the cylinder axis 68 and converges with the vertical line. With it the cylinder axis 68 is located close to the center of the entrance opening 3. The cylinder 64 has been attached at the driving axis 94 by means of a fastening ring 96 and with the aid of a rod arrangement 98 which diverges in a star-shaped mode from said ring 96.

During the examination of a patient the driving motor is operated in the forward drive mode (up to $+360°$) and in the reverse mode (up to $-360°$). By means of ultrasound coupling, the radiation surface 82 of the ultrasound array 12 lies against the flexible foil 74 within the lower container 66. In this instance, the radiation surface 82 is directed toward the upper fluid container 62 and in particular toward the breast to be examined 4. During the operating mode of the driving motor 92, the cylinder 64 below breast 4 rotates continuously around the cylinder axis 68, and the radiation and receiving surface 82 of the ultrasound scanning head describes a cone-shell shaped scanning path. The organ to be examined 4 is therefore scanned in the ultrasound mode from every angle position.

Located at the lowest part of the upper container 62, a drain 100 in the form of a spout with a closing apparatus enables water to enter or to be drained off. In order to channel the ultrasound conducting fluid in the direction of the inlet and draining device 100, a guide piece has been arranged adjacent to the ring 76.

In FIGS. 6 and 7 the sample embodiment of a supplementary configuration for a commercial realtime ultrasound examination device includes several advantages. This embodiment includes only one cylinder 64 to form on one hand the fluid container which is now upper container 62 and on the other hand the safety area for the ultrasound as well as for its supports 84, 86, 87. The ultrasound array 12 is located outside the water-filled basin, so that after easy detachment from the angle brackets 84, 86, it can be removed through the cylinder opening 90 and used for other examination purposes. Equally advantageous is the restriction of the ultrasound coupling to the area of the ultrasound array 12. It is located in the floor 72 of the rectangular recess of predetermined size which corresponds to the size of the radiation surface 82. As an additional advantage, the inlet and draining device 100 for the liquid can be arranged at the lowest part of the upper container 62. Also, it is, advantageous, that the construction of the supplementary device is of easy realizable nature.

Figure 8:
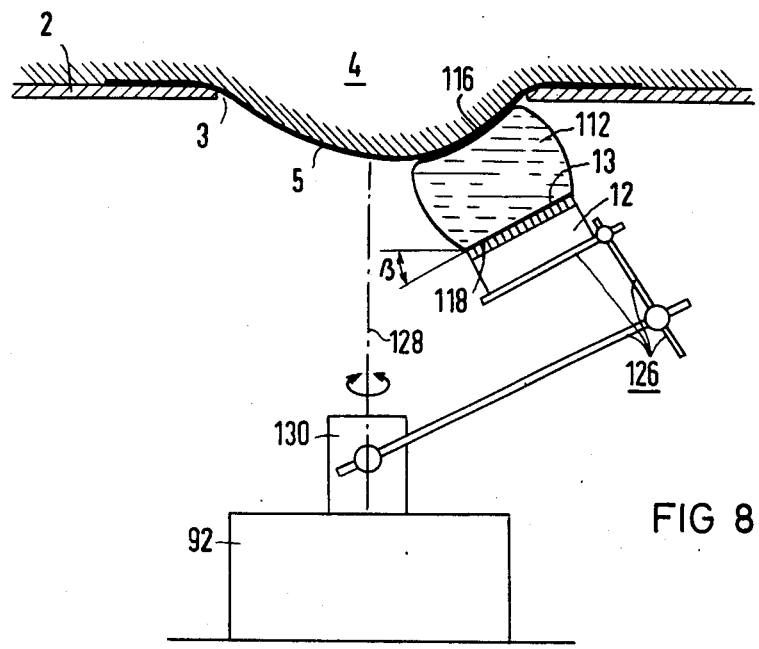
FIG. 8 shows a fifth sample embodiment with an enclosed fluid bag.

FIG. 8 provides a further supplementary configuration for a commercial realtime ultrasound examination device (not shown). This embodiment has been especially designed for mamma examinations.

According to FIG. 8, the cover board 2 has been provided as before with an entrance opening 3. Again, the entrance opening 3 is covered with a membrane 5. As before, rubber foil is preferred as material for the membrane 5. With this embodiment a contact gel is located between the compressed breast 4 of the patient which again lies directly against the membrane 5. In turn the membrane 5 separates the body part from the device.

At the device side of the membrane 5 a fluid bag has been provided. This bag is a completely closed bag or sack of flexible material, which has been filled with a suitable liquid such as water for efficient ultrasound conducting. The bag 112 consists of a an expandable skin, i.e. rubber skin or some other kind of flexible foil. It also posesses a flexible front face, which has been designed as a gliding plane, and an opposite backside 118, which is used as contact surface. The surface area of the front and backside 116 and 118 is essentially parallel to the radiation surface 13 of the ultrasound probe or ultrasound array 12. The contact surface 118 is coupled in a removable and ultrasound transmitting mode to the radiation surface 13. However, while the flexible gliding plane is also coupled in an ultrasound mode to the membrane surface, it merely lies against said membrane. FIG. 8 elucidates, that bag 112 is not taut with liquid. Instead the bag is filled with a moderate body of liquid, so that the gliding plane 116 with the breast 4 lying against the membrane 5 adjusts itself to the form of the membrane and consequently to the contour of the breast. As seen, the gliding plane 116 has therefore a convex form.

Between the membrane 5 and the fluid bag 112 a contact gel or another adhesive medium has been provided, which acts at the same time as gliding substance.

As already mentioned, a conventional ultrasound transducer for realtime examinations according to the pulse/echo principle is located on the backside of the bag 112. Again, a contact gel has been provided between the backside and the ultrasound transducer. The ultrasound array 12 and the bag 112 are connected in a removable manner. The ultrasound array 12 as such as been attached in a removable manner on a support configuration 126. As described in FIG. 3, this support configuration 126 can be designed as rods, which are connected through adjustable links.

The ultrasound array 12 and its support configuration 126 can be rotated around a preferably vertical rotation axis 128. For that purpose, the support configuration 126 is arranged at the shaft 130 of a driving motor 92. It is also important, that the radiation surface 13 is arranged in a slanted and not parallel position to the vertical rotation axis 128 and here in particular to the horizontal. The adjustable angle between the horizontal and the radiation surface 13 is identified with B. Preferably, this tilting angle is approx. 20°. Again it has to be emphasized, that many application cases can be served with such an adjustment.

Again, the driving motor 92 will perform a continuous rotation, whereby a rotation range of +/−180° or +/−360° can be specified. When rotating the shaft 130, the front or the gliding plane of the bag 112 glides along the outside of the membrane 5, while the ultrasound array 12 scans the breast 4 with ultrasound in the real-time procedure.

The embodiment shown in FIG. 8 requires a fluid bag 112 of a relative small liquid volume. The liquid volume is enclosed from all sides, so that no overflow can occur. Also, in this embodiment the coupling with ultrasound is essentially limited to the area of the ultrasound array 12. Again, subsequent to the appropriate adjustment, the radiation surface 13 of the ultrasound array 12 is in an essentially parallel position to the scanned breast surface.

It should be emphasized once more, that the fluid bag 112 is only moderately filled with an efficient ultrasound conducting liquid and designed in a manner to ensure that the flexible gliding plane 116 receives a convex form during the adjustment process to the breast 4. FIG. 4 shows how such an embodiment can be achieved, while ensuring at the same time a stable securing mode.

Figure 9:
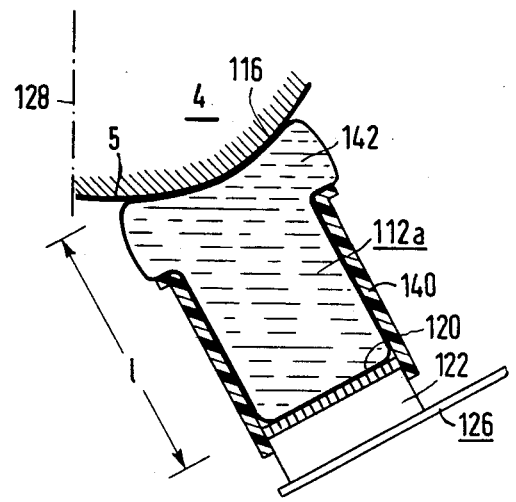
FIG. 9 provides a modification of the enclosed fluid bag according to FIG. 8.

According to FIG. 9, the fluid bag 112 is situated in a support container 140. Essentially this support container 140 is a casing adapted to the shape of the head. The largest part of the liquid-filled bag 112 is contained in this casing. This casing has a mushroom-like appearance, because of the enlarged front or head part 142, which receives this expanded form due to the pressure against the breast 4. With it, the gliding plane 116 is of course released from the support container 140. As a result, the gliding plane 116 will receive a concave form again. As previously, the gliding plane 116 glides during actual operations over the membrane 5, which compresses the breast 4. The support container 140 can be manufactured from any material, i.e. synthetics or plexiglas. Preferably, the support container 140 should be attached in a removable mode at the ultrasound array 12. This can be provided insofar as the back part of the support container 140 encloses the front part of the ultrasound array 12. In this case, the ultrasound array can be removed in a relatively easy manner from the contact surface 118 of the liquid-filled bag 112 and used for other application purposes.

It has been shown, that the distance 1 should be to approx. 5 to 6 cm (FIG. 9) between the radiation surface 13 of the ultrasound array 12 and the gliding plane 116 of the mushroom-shaped head part 142, if the slice center of the examined tissue of the breast 4 is to be placed in the focus line of the ultrasound array 12.

The sample embodiments shown in FIGS. 8 and 9 combine the advantage of an enclosed liquid volume with the advantage of a limited ultrasound coupling surface. It should be also noted, that a relative simple construction is used. As previously, the radiation surface 13 rotates on a cone shell around the body part to be examined.

There has thus been shown and described a novel ultrasound examination device which fulfills all the objects and advantages sought therefore. Many changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. A device for adapting ultrasound examination apparatus which includes an ultrasound array having a radiation surface to dedicated scanning of specific body parts such as testicles and female breasts, comprising:
    (a) a fluid container containing an ultrasound conducting fluid and having an external ultrasound coupling surface;
    (b) support means for detachably securing the ultrasound array to said coupling surface in a manner that said radiation surface is at an angle with respect to a substantially vertical axis of rotation; and
    (c) rotation means for rotating said support means and said ultrasound array around said axis of rotation, whereby said radiation surface rotates on a conical path around the body part to be scanned and said body part is scanned from a plurality of directions.

2. An ultrasound examination device as in claim 1, wherein said fluid container is stationary with respect to said body part and wherein said second container and said ultrasound array rotate around said axis of rotation.

3. The device of claim 1, wherein said support means includes a second container surrounding said ultrasound array, said second container being free of liquid when in use and being rotatable around said axis of rotation, and wherein said ultrasound array, coupled to said coupling surface, is linked to the second container and rotatable therewith.

4. An ultrasound examination device as in claim 3, wherein said second container and said fluid container are arranged to share said rotation axis and wherein said ultrasound array is coupled to said fluid container and rotates together with said second container and said fluid container around said body part.

5. The device according to claim 3, wherein said second container further comprises a collecting container located at the upper perimeter of said second container to collect overflowing ultrasound conducting liquid from said fluid container.

6. The device according to claim 5, wherein said collecting container is a groove running along the upper edge of said second container.

7. The device according to claim 5, wherein said collecting container is an inflatable ring made of rubber which is arranged in a concentrical mode to an opening of said fluid container and which prevents spillage of ultrasound conducting liquid from said fluid container and which further serves as a soft positioning surface for said body part.

8. An ultrasound examination device as in claim 3, which further comprises a membrane of predeterminable flexibility for positioning said body part thereon, said membrane being arranged above said fluid container so that said membrane is stretched and extended into said fluid container by said body part.

9. The device as in claim 8, wherein said membrane is sufficiently perforated so that overflowing ultrasound conducting liquid contained in said fluid container can pass therethrough.

10. The device of claim 8, wherein said membrane directly covers the opening of said fluid container.

11. The device of claim 3, further comprising:
(a) a cover board, installed with a patient table, having an entrance opening; and
(b) an opening at the upper end of said fluid container, said entrance opening being arranged so that it lies above said opening of said fluid container.

12. The device of claim 11, wherein said second container and said fluid container are supported on a floor base so that the opening of said fluid container is located under and in proximity to said entrance opening of said cover board.

13. The device of claim 11, wherein said second container and said fluid container are located on an auxiliary shelf which is attached to said cover board in a suspended mode so that the opening of said fluid container is located under and in proximity to said entrance opening of said cover board.

14. The device of claim 11, wherein the upper edge of said second container is attached in a rotating mode to said entrance opening of said cover board by means of a ring shaped bearing.

15. The device as in claim 3, wherein said rotational means comprises:
a rotation drive attached to said second container at its lower perimeter, said rotation drive being operative to rotate said second container around said axis of rotation.

16. The device of claim 3, wherein said second container is designed in the shape of a funnel.

17. The device as in claim 3, wherein said support means include:
a U shaped support rail, said support rail being operative to hold and support said ultrasound array in a coupled mode to said fluid container; and
a support rod comprised of several rod parts which are linked by cross joints, connected to said support rail, said support rod further having a lowest part which is attached by means of a swivel joint to said rotation means.

18. The device as in claim 3, which further comprises a slot or opening in the wall of said second container through which said ultrasound array may be introduced into or removed from said second container.

19. The device as in claim 1, wherein said fluid container is designed in the form of a totally enclosed fluid bag, said fluid bag having a gliding plane facing said body part and a contact surface for coupling, in a removable mode, said liquid bag to said ultrasound array.

20. The device as in claim 19, wherein said fluid bag is constructed of flexible material.

21. The device as in claim 19, which further comprises a support container, said support container serving to support and contain within its inner space the largest part of said fluid bag which does not include said gliding plane of said fluid bag, said support container further including, at its backside, an efficient ultrasound coupling surface for coupling said ultrasound array thereto.

22. The device according to claim 1, wherein said rotation means include an electrical motor.

23. The device according to claim 1, wherein said fluid container is a cylinder body said cylinder body having a vertical cylinder axis and including:
a slanted liquid resistant separation wall with an ultrasound coupling surface, to divide said cylinder body into an upper and lower container, whereby said upper container is designated to receive and hold said ultrasound conducting fluid and whereby said ultrasound array is removably supported within said lower container at said ultrasound coupling surface of said separation wall.

24. The device as in claim 23, wherein said separation wall is slanted at angle of between 65° and 75° with respect to said vertical axis.

25. The device according to claim 23, wherein said separation wall is constructed of an elastic foil supported on a firm base, said firm base having a recess to receive said ultrasound array so that the radiation surface of said array lies against said foil.

26. The device according to claim 25, which further includes an elliptic fastening ring to secure said elastic foil at its perimeter to said base of said separation wall.

27. The device according to claim 23, which further comprises a drain for the evacuation of said ultrasound liquid from said upper container, said drain being located at a point on a wall of said cylinder body and near a lowest part of said separation wall.

28. The device according to claim 23, which further comprises:
a cover board, installed with a patient table, having an entrance opening; and
a flexible membrane covering said entrance opening, said cover board being arranged above said cylinder body so that said body part, to be examined, may stretch said membrane and be extended with it into said upper container of said cylinder body.

29. The device as in claim 23, wherein said support means includes a star-shaped rod arrangement said rod arrangement being connected to said cylinder body at its outer end and supported and linked to said rotation means at its center so that said cylinder body is rotatable around said body part.

30. The device as in claim 23, wherein said rotation means include an electrical motor.

* * * * *